(12) United States Patent
Gombinsky et al.

(10) Patent No.: US 6,409,925 B1
(45) Date of Patent: Jun. 25, 2002

(54) DEVICE AND SYSTEM FOR TRANSFER OF MATERIAL

(75) Inventors: Moshe Gombinsky, Bat-Yam; Anna Khatskina, Ariel, both of (IL)

(73) Assignee: Bio-Magnetics Ltd., Bat-yam (IL)

( * ) Notice: Subject to any disclaimer, the term of this patent is extended or adjusted under 35 U.S.C. 154(b) by 0 days.

(21) Appl. No.: 09/601,741

(22) PCT Filed: Feb. 5, 1999

(86) PCT No.: PCT/IL99/00078
§ 371 (c)(1),
(2), (4) Date: Aug. 7, 2000

(87) PCT Pub. No.: WO99/40444
PCT Pub. Date: Aug. 12, 1999

(30) Foreign Application Priority Data

Feb. 6, 1998 (IL) ................................. 123210

(51) Int. Cl.[7] .......................... B01D 35/06; B01D 24/00; B03C 1/100; G01N 33/536

(52) U.S. Cl. ..................... 210/695; 210/222; 210/416.1; 209/224; 209/232; 436/526; 435/6

(58) Field of Search ................................. 210/695, 222, 210/416.1; 435/6; 536/24.3, 526; 141/130; 719/217; 436/256; 219/225; 209/224, 232

(56) References Cited

U.S. PATENT DOCUMENTS

| | | | | |
|---|---|---|---|---|
| 4,056,258 A | | 11/1977 | Papoff et al. ................ | 366/160 |
| 4,292,920 A | | 10/1981 | Smith et al. ................. | 118/425 |
| 4,598,840 A | | 7/1986 | Burg ......................... | 222/135 |
| 5,288,468 A | | 2/1994 | Church et al. ............... | 422/116 |
| 5,567,326 A | | 10/1996 | Ekenberg et al. ............ | 210/695 |
| 5,647,994 A | * | 7/1997 | Tuunanen et al. ........... | 210/695 |
| 6,044,876 A | * | 4/2000 | Ally et al. ................... | 141/130 |

FOREIGN PATENT DOCUMENTS

| | | | |
|---|---|---|---|
| EP | 0 601 213 | | 6/1994 |
| EP | 0 810 438 | | 12/1997 |
| WO | WO 86/06493 | * | 11/1986 |
| WO | WO 87/05536 | * | 9/1987 |
| WO | WO 96/12958 | * | 5/1996 |
| WO | WO 97 43 447 | | 11/1997 |

OTHER PUBLICATIONS

Pourfarzaneh et al., "The Use of Magnetizable Particles in Solid Phase Immunoassay", Methods of Biochemical Analysis, 1982, v. 28, pp. 267–295.

Lacheumeier et al., "A New Approach To Template Purification For Sequencing Applications Using Paramagnetic Particles". Biotechniques. 1992, pp. 124–131, v. 13, N. 1.

Uhlen, M., "Magnetic Separation of DNA". Nature, Aug. 31, 1989, pp. 733–734, v. 340.

Philip Day et al., "Immobilization Of Polynucleotides On Magnetic Particles: Factors Influencing Hybridization Efficiency", Biochem, 1991, pp. 735–740, v. 278.

Kit Lam et al., "A New Type Of Synthetic Peptide Library For Identifying Ligand–Binding Activity" Nature, Nov. 7, 1991, pp. 82–84, v. 354.

Jeffery Jacobs et al., "Combinatorial Chemistry–Applications Of Light–Directed Chemical Synthesis" Tibtech, Jan. 1994, pp. 19–26, v. 12.

Valerio, Robert et al., "Synthesis Of Peptide Analogues Using The Multipin Peptide Synthesis Method", Analytic Biochemistry. 1991, pp. 168–177, v. 197.

* cited by examiner

Primary Examiner—Kenneth R. Horlick
Assistant Examiner—Alexander H. Spiegler (57) ABSTRACT

The invention concerns a device for collection of magnetic particles. The invention further concerns a system for transfer of material from a plurality of source vessels to a plurality of target vessels, the device comprising a plurality of collecting members each of which can be manipulated independently. The invention further concerns a method for detection of biological entities being fluorescent label, wherein the entities are bound to magnetic particles. The fluorescent emission is concentrated by clustering the magnetic particles utilizing magnetic force.

8 Claims, 9 Drawing Sheets

44+47
Exp.

DEVICE AND SYSTEM FOR TRANSFER OF MATERIAL

CROSS REFERENCE TO RELATED APPLICATION

The present application is the national stage under 35 U.S.C. 371 of PCT/IL99/00078, filed Feb. 5, 1999.

FIELD OF THE INVENTION

The present invention concerns a device and system for the transfer and/or manipulation of liquids or particles. The present invention further concerns a method of detection of biological entities using magnetic particles.

BACKGROUND OF THE INVENTION

In recent years, with the advance of automatization in laboratory techniques, many assays, reactions, diagnostic procedures and synthesis techniques, are carried out by the transfer of a plurality of liquid samples, simultaneously, from one array of liquid-containing wells to another. Typically, these are arrays of 5, 8, 16, 25, 96, 384, or 1536 liquid-containing wells. In order to transfer, add, collect or mix liquids, or particles to present in all the wells in the array simultaneously, various multi-collector systems have been devised. The most commonly used is a multi-pipetor which collects liquid from an array of source wells to an array of target wells, simultaneously, by application or release of application, respectively, of vacuum force. However, in all known multi-pipetor devices, each individual pipetor capable of collecting or releasing liquid from the well is connected by vacuum force to all other pipetors so that all samples in the well are collected and released at once (Valerio et al., *Analytical Biochemistry*, 197:168–177 (1991)).

Magnetic particles are used for a variety of separation, purification, and isolation techniques in connection with chemical or biological molecules. In those techniques, a magnetic particle is coupled to a molecule capable of forming a specific binding (hereinafter "affinity binding") with a molecule in a biological sample, which is to be isolated, purified or separated. The biological sample is then brought into contact with the magnetic particle and those biological molecules which bind to the magnetic particles are then isolated by application of a magnetic field.

Such magnetic separation techniques have been employed to sort cells, to recover antibodies or enzymes from a solution, to purify proteins using affinity techniques, and to remove unwanted particles from suspension, for example, to remove cancer cells ex vivo, from a cell preparation which is then injected into a patient (Pourfarzaneh, M. et al., "*The use of magnetizable particles in solid phase immunoassay in methods of biochemical analysis*" 28:267–295 (1982)).

For the purpose of using magnetic particles, various devices have been developed in order to transfer the magnetic particles from one location to another, for example from one reaction vessel to another reaction vessel.

U.S. Pat. No. 4,292,920 discloses a device for transferring, by bio-magnetic attraction, antigen-antibody adsorbent material from one reaction mixture to the other. The device may comprise a single or multipin arrangement, corresponding to a well arrangement, which is capable of attracting by magnetic force magnetic particles. By one embodiment, the pin is connected to an electromagnet, and by turning the electromagnet on and off the pin becomes magnetized, or non-magnetized, respectively.

U.S. Pat. No. 5,567,326 discloses an apparatus and method for separating magnetically responsive particles from a nonmagnetic test medium in which they are suspended. The device comprises a plurality of nonmagnetic pins (termed "magnetic field directing elements") arranged in an array, and a magnet positioned normal to said array. Placing the magnet on the array of pins, renders all the pins in the array magnetic causing particles to be attracted to them, and thus collecting them; and removing the magnet causes the pins to become non-magnetic, and consequently the magnetic particles are released from the pins.

The drawbacks of the above devices and apparatuses reside in the fact that the magnetic pins come into direct contact with the magnetic particles, so that if rinsing and sterilization is required, the whole apparatus or device has to be washed which procedure is expensive and time consuming. Furthermore, the collection of particles is not efficient since in such a construction, due to surface tension forces, some of the particles remain in the suspension.

Another drawback of the prior art devices reside in the fact that where a multi pin device is used to collect magnetic particles from a plurality of wells, the particles from all the wells have to be collected at once in an "all or none" fashion, and it is not possible to selectively collect particles only from some wells in an array.

Magnetic particles were also used for detection purposes, for example for DNA purification for detection purposes, using a method similar to reverse hybridization blot system. However here the specific oligonucleotide probe was attached to a paramagnetic particle instead of a sheet membrane. The target DNA, which contains the complementary sequence of the probe, hybridizes to the probe that is attached to the bead and is then magnetically removed from the solution, washed and collected (Fry et al., *Bio Techniques*, 13(1) 124–131 (1992)). Coupling of the polynucleotides to the magnetic particles can be carried out for example according to the teaching of Day et al. (Biochem. J. 278, 735–740 (1991)). Immobilization of nucleic acid sequences on magnetic beads can also be carried out utilizing the streptavidin—bioten technology (Uhlen M., Nature, 340, 773–739 (1989)).

GLOSSARY

The following terms will be used at times throughout the specification:

"Material"—the contents of a vessel which is tranferred from a first plurality of vessels termed "source vessels" (see below) to a second plurality of vessels termed "target vessels" (see below). Typically, a "material" is a small amount of liquid, solid particles (such as beads), for example contained in a liquid or magnetic particles.

"Plurality of vessels"—two or more material-holding vessels. The plurality can be present in one "array of vessels" (see below), for example each plurality may be a line or column in a single array. Alternatively, the plurality may be the array of vessels itself for example a 96-well array.

"Array of vessels"—a plurality of voids present in a single construct which holds the material. Typically the array of vessels is an array of wells. State of the art wells have an 8, 16, 25, 96, 384 or 1536—well arrangement.

"Source vessels"—a plurality of vessels from which material is collected.

"Target vessels"—a plurality of vessels to which material is released.

"Transfer"—an action of withdrawing and holding (i.e. collecting) the material from one plurality of vessels (source) and releasing the material to another plurality of vessels (target).

"Collecting member"—a component of the system of the invention capable of collecting (upon activation) and releasing (upon deactivation) material from a single vessel for example from a single well. The system comprises a plurality of individual collecting members each capable of being activated and deactivated independently.

"Activated state" ("activated") "deactivated state""Deactivate"—a change of property of the individual collecting member which can cause it to collect or release material, respectively, for example, by application and removal of vacuum force. Another example is creation of an activated state by placing a magnetic-field providing member in a fist position where it is present at the distal-collecting end of the device and deactivated state is created by moving said member to a second position where it is spaced from said distal-collecting end. In the first position magnetic particles (the material) one collected and in the second position magnetic particles are relevant. Another option is a collecting member comprising an electromagnet when the electromagnet is turned on, magnetic particles are collected and the collecting member is the activated state. When the electromagnetic is turned off, the magnetic particles are released and the collecting member is in the deactivated state.

"Manipulation"—a collection and release of magnetic particles resulting in their transfer from one location to the other as well as the movements of the particles within a medium for various purposes for example, for mixing them with various reagents, for rinsing etc.

"Magnetic particles"—particles of various sizes, comprising a magnetic substance, being a substance which is either a magnet, i.e. having a 'magnetic memory' or a substance which is not a magnet but is attracted to magnets, i.e. a ferromagnetic material. The magnetic particles may consist solely or essentially of the magnetic substance. Alternatively, the magnetic particles may be composite particles comprising the magnetic substance and other non-magnetic substances such as agar, agarose, non-magnetic metal, glass, nitrocellulose, etc. The composite particle may either consist of a core or be made of the magnetic substance and a shell made of the non-magnetic substance or may comprise several sub-particles made of the magnetic substance embedded in the non-magnetic substance. The term "magnetic particles" is to be understood as encompassing also the so-called "magnetic beads" or "magnetic microbeads" used in the literature.

SUMMARY OF THE INVENTION

The present invention of the first aspect termed "the system aspect" concerns a system for transfer of material from source vessels to target vessels such that material from each source vessel is transferred to a designated target vessel, the system comprising a plurality of collecting members permitting simultaneous transfer of material from a number of source vessels to one or more target vessels, each collecting member having an activated state for withdrawing and holding material contain in a source vessel and a deactivated state in which any material held thereby is released, transition from an activated state to a deactivated state of each collecting member is independently controlled.

The source vessels and target vessels may belong to the same array, for example, the source vessels may be a first line of 12 wells in a 96-well arrangement and the designated target vessels may be the second line. Alternatively, the source vessels may be all wells in one array (for example all 96 wells in a 96-well arrangement) and the target vessels all the wells in another array of vessels.

The system of the present invention, may further comprise a control device, such as a computer, and/or a computer controlled robot, which enables the individual activation and deactivation of each collecting member of the system.

The selective collection of material from some vessels present in a plurality of vessels, for example, in a 384-well arrangement, may be useful in various automatic laboratory procedures, (as will be explained below). Selective collection and release of material by some individual collecting members may be determined by giving x and y axis parameters of the specific collecting member to be activated or deactivated to a computer/robot.

If desired, the individual collecting members of the system may be detachably connected to a frame holding them together, so that individual collecting members may be detached and either used separately or in another system. For example, in sequencing by hybridization techniques or combinatiorial chemistry, several devices from the system may be detached, fitted to a smaller frame creating a smaller array of individual collecting members. This procedure may be repeated again and again so that each time only those collecting members which collected particles with hybridized sequences are collected and rearranged in new and smaller arrays.

The individual activation of each collecting member has an advantage in some laboratory experimental and diagnostic procedures, and in general allows greater flexibility of the process.

For example, at times a large array of wells containing various reagents is prepared in advance for carrying out various detection assays, for example, for detection of infectious agents or genetic diseases in a plurality of samples. Large laboratory centers buy these arrays of reagents-containing wells in advance. However, at times, for example in a given day, the number of specific samples. to be diagnosed, may be smaller than the number of wells present in the well array. If a state-of-the-art multi-pipetor is used, due to the "all or none" mode of its activation (all individual pipetors in the device are activated at once), all the reagent-containing wells which are not used for assaying the samples, are nevertheless manipulated by collection and transfer, and are in fact contaminated and wasted. Such a procedure which is repeated many times during the course of a day, in a plurality of different reagent wells, causes a vast waste of expensive reagents. By use of the system of the invention, it is possible to program that only some of the wells are used, for example, if only 50 samples are to be diagnosed and the array is of 96 wells, then it is possible to program collection only from the first 50 wells and the other 46 wells remain intact for future use.

Another use of the system of the present invention, is in combinational chemistry, for example, for the preparation of short peptides or nucleotide sequences. Today, the most widely used technique for combinational chemistry is the "mix-and-split" technique, wherein the pool of solid-phase, non-magnetic beads, on which a synthesis should occur, is divided to two or more parts. To each part a different chemical moiety, for example amino acid, is added, and then the two parts are repooled, i.e. are combined again together ("mix"), redivided ("split"), and again to each individual pool a different amino acid is added. These steps are repeated again and again. Since in each step, the different pools of peptides which are being synthesized, are mixed, divided, and to each part a different amino acid is added, by using several elongation steps, a huge variety of different combinations of peptides is created. For example if each time the pool is divided into 2 parts, then after n steps of mix-and-split, $2^n$ different species of synthesized molecules are prepared. However, the problem is that all these different species of peptides are present in one mixture, and a large effort in this combinatorial chemistry technique is required in order to isolate the peptides of interest (Lam et al., *Nature*, 354:82–84 (1991); Jacob et al, *Tibtech*, 12:19–26 (1994)).

Against this, by use of the system of the invention, it is possible to start with an array of wells, wherein each well contains a different chemical moiety serving as a building unit (such as one species of amino acid, one species of nucleic acid, or chemical moiety) to be added, to the molecule synthesized by the combinatorial methods. It is a priori known which compound is present in each well. A first building unit of species X (amino acid) may be added by using the system of the invention only to half the wells in the array. A first building unit of species Y may be added to the second half of the wells. Then a second building unit of species Z may be added to half of the X-containing peptide and to half of the Y-containing peptide, and a second building unit of species T may be added to the other half of the X- containing species and the Y- containing species. This results in 4 types of di-peptides: X-Z, X-T, Y-Z, Y-T. Two altered species of a third building unit can be added again each time to half of the above di-peptides increasing the number of different peptides to $2^3$ (8). In general, the number of different combinations in $A^P$, wherein A is the number of different amino acids used and P is the length of the peptide. As can be seen, a large number of different combinations of peptides is created by adding each time a different amino acid to each half of the elongating molecule, so that if each time a new amino acid is added to half of the samples, after n step $2^n$ different combinations are created. If instead of dividing the species to two parts, the species are divided to four parts, then after n step $4^n$ different combinations are created. However, by use of the system of the invention, at the end of the synthesis process it is well known in which well each final combination (i.e. each polypeptide) resides. So, that although the number of different combinations while utilizing the system of the invention is as large as in the mixed-and-split method, there is no need to invest time in isolating each specific species from among the other, since each specific polypeptide is present in a separate well.

By one embodiment, termed "the magnetic embodiment", the material to be collected or released is magnetic particles and the collecting members are capable of transferring the magnetic particles by magnetic force. By another embodiment termed the "non-magnetic embodiment", the collecting members transfer the material by forces other than magnetic force, for example by vacuum force.

The arrangement and spacing of the individual collecting members in the system of the invention should correspond to the arrangement and spacing of the array of vessels (for example wells) from which the materials are collected and/or to which they are released.

For example in the "non magnetic aspect" the system may provide a plurality of pipetors, each capable of application of vacuum force independently. This may be carried out for example by raise of each piston of the pipetor independently using miniature, robot-control servo-mechanism; Alternatively the raise of the piston of the pipetors may be carried out using magnetic force or by simultaneous application of vacuum force on all pipetors at once but isolating individual pipetors from the vacuum force by activation of independently closing sealing means in some individual pipetors, so that they are isolated from the universally applied vacuum. By such an arrangement material is not collected by these individual collecting members.

By another aspect termed "the device aspect" the invention concerns an individual collecting member which is suitable for transfer and manipulation of magnetic particles. The device may be used separately or as a part of the system of the invention.

Thus the present invention concerns a device for the manipulation of magnetic particles, being particles which are attracted by magnetic force, the device comprising:

an elongated member made of a material which is not affected by a magnetic field, having a particle collecting tip and an elongated lumen with an end, said end of the lumen being at a distal portion of said elongated member adjacent to said tip; the lumen slidable accommodating a magnetic field providing member displayable between a first position in which the magnetic field providing member is in said distal portion whereby attraction of said particles to said tip occurs, and a second position in a proximal portion of said lumen in which said particles are not attracted to said tip.

The use of magnetic particles in which the magnetic substance is ferromagnetic is generally preferred, for example, particles made of superparamagnetic iron oxide. Such particles are capable of responding well to relatively weak magnetic fields, but have essentially no magnetic memory, that is once the magnetic field is removed they do not maintain magnetic attraction forces.

The elongated member in accordance with the device aspect is made of a material which is not affected by a magnetic force, i.e. a non-magnetic non-ferromagnetic material, for example, plastic, glass, various synthetic polymers such as polypropylene and the like.

The member has an open-ended or close-ended particle collecting tip, which is the part which comes into contact with the particles and can collect them by magnetic force. Preferably, said tip is replaceable, or is covered by a replaceable cover, so that after contact with the particles and the reaction mixture it can be replaced by a clean or sterile tip or cover. This construction enables easy and inexpensive sterilization of the device.

Extending inside the elongated member is an elongated lumen having an open or a closed end. If the lumen is open its opening should be of a size which does not allow the field provided member to protrude therefrom. Said end is at a distal part of said member and close to its particle collecting tip.

The lumen accommodates a slidable magnetic field providing member, which may be completely composed of a magnet; may be made of a magnetic as well as a ferromagnetic material or made of a material which can become magnetized by an electromagnet, but has no magnetic memory. The member can also comprise an electromagnet with or without a magnetizable core. Such a magnet allows to apply a precise magnetic force for collection of precise amounts of magnetic particles for quantitative or semi-quantitative collection.

The slidable magnetic field providing member may move between two positions: a first position where the member is at the distal end of the lumen and hence adjacent to said particle collecting tip, and a second position wherein the member is outside of the distal end of the lumen and hence distanced from the particle collecting tip.

In said first position (the activated state), since the magnetic field providing member is adjacent to said tip particles are attracted to the tip and in said second position (deactivated state), since the member is distanced from said tip, particles are not attracted to the tip, or particles which were previously attracted are released.

The particle collecting tip has a size which is adapted for the specific usage of the device, for example, where the device is used to collect particles from a well, it should be of the size of a tip of a standard pipetor.

By one option the tip has tapering sides and a truncated end. A truncated end is preferable since it ensures that the magnetic particles are not attracted in large clusters to the tip, since such large clusters are released easily from the tip and thus it is difficult to transfer all the particles. The truncated end also eases quantitative or semi-quantitative collection of magnetic particles. By another option the tip's sides do not taper at all and are parallel right to their end creating a cylinder shape.

The material of the tip, or of the disposable cover covering the tip, should be of the type and construction as to avoid maintenance of the particles by adherence, adherence or absorbance thereto, i.e. a non-porous material. As indicated, either the tip is replaceable, or the tip has a cover (similar for example to the plastic tip of an automatic pipetor) which is replaceable. An example of a tip or a replaceable cover are made of polypropylene.

The magnetic field providing member is preferably elongated.

By a preferred embodiment, the body of the field providing member is an elongated magnetic rod, and the end of the rod may be tapered or cylindrical and made of a ferromagnetic material, such as iron or magnet. The purpose of the iron tapering end is to focus the magnetic field produced by the magnetic rod.

The field providing member may be displaced between the two positions manually and for this purpose the field providing member should be fitted with a handle.

Alternatively and preferably, the field providing member may be displaced automatically, for example, by a computer-controlled mechanical device, or by the aid of a computer-controlled pneumatic pump. The member may also be displaced by the use of an electromagnet, which when turned on, attracts the member to said second position, and when tuned off does not attract the member so that it can fall by gravity force, into said first position when the device is held normal to the vessel.

The system of the invention according to the magnetic embodiment may comprise a plurality of individual devices of the invention. The system may comprise any number of devices such as five, eight, ninety-six, etc. (preferably multiples of ninety-six or of 5, 8 or 12), for the simultaneous manipulation of magnetic particles, for example for the simultaneous transfer of magnetic particles present in an array of reaction vessels to another array.

The magnetic field providing members of the individual devices constituting the system of the invention may be connected to each other so that they can be displaced, manually or automatically all together. However, it is preferable that the displacement of each individual device constituting the system may be carried out independently so that it is possible to displace some devices or collecting members in the system while not displacing others. Such an arrangement can enable the collection of magnetic particles from some wells in an array of reaction vessels while magnetic particles from other wells are not collected. Selective collection from specific wells may be useful in various laboratory procedures such as sequencing by hybridization (SBH) or combinatorial chemistry.

By another embodiment of the present invention the magnetic field providing member is stationary inside the elongated member. The magnetic field providing member is either connected to an electromagnet or comprises an electromagnet. By turning the electromagnet on and off the member becomes magnetized and non-magnetized and magnetic particles are attracted and released from the particle collecting tip, respectively, without any requirement of movement inside the elongated member. Such a device can also be part of the system of the invention, i.e. the electro magnets of each collecting member are turned on or off independently from the other electromagnets so that each collecting member is activated or deactivated individually.

By another aspect, to "the detection aspect" the present invention concerns a method for the detection of biological entities carrying a fluorescent label, in a sample, the method comprising:

(i) Providing magnetic particles which can specifically bind to said biological entities;

(ii) Contacting the magnetic particles with said biological entities under conditions allowing said specific binding;

(iii) Clustering the magnetic particles by magnetic force, thereby causing fluorescent emission to become concentrated in distinct patches;

(iv) Reading said fluorescent emission, reading above control level indicating the presence of the biological entities in the sample.

The method of the present invention is for detecting any type of biological entities which may become any type of molecule, complexes of molecules, or cells present in biological tissues. Examples are proteins, peptides, amino acid sequences, nucleic acids sequences, hormones, enzymes, receptors, ligands, polysaccharides and the like, as well as molecules which are laboratory produced and which are intended to be similar to biological molecules obtained from natural sources, such as laboratory produced synthesized peptides, oligonucleotides synthesized by laboratory, for example by PCR methods, antibodies and the like. The term biological entities also concerns cells, viruses, plasmids, and various cell organels such as mitochondria, denucleos, etc.

The sample may be any type of liquid media containing the biological entities which are to be detected. The sample may be obtained from a biological source, or may be the result of a laboratory manipulation such as, for example, a result of a PCR amplification of nucleic acid sequences. The biological entities to be separated are of the type which carry a fluorescent label. The fluorescent label may be introduced to the biological entity, which is laboratory produced, during the synthesis procedure. For example, when synthesizing nucleic acid sequences utilizing PCR, some nucleic types used in the synthesis may bear a fluorescent label. Another example is amino acid sequences synthesized on a machine, which are synthesized while using some fluorescently labeled amino acid building units.

Alternatively, the biological entities may carry a fluorescent label, by reacting them with other molecules which carry said label. For example, where the biological entity is a protein, it may be reacted with an antibody carrying a fluorescent label. Where the biological entity is a receptor, it may be contacted with a ligand carrying a fluorescent label and the like.

The particles, according to the method of the invention, are capable of specifically binding to the biological entities. The specific binding, is typically carried out by attaching to the magnetic particle one member of the pair forming group while the other member of the pair forming group is the biological entity to be detected. For example, if the biological entity to be detected is a nucleic acid sequence, then the magnetic particle should carry the complementary sequence, where the biological entity is a protein, the magnetic particle should carry a specific antibody, where the biological entity carries a biotin, or streptavidin moiety, then the magnetic particle should carry the streptavidin, or biotin complementary moiety, respectively. Other examples of a pair forming group are a receptor and its ligand, an enzyme and its substrate, a lectin and its specific glycoprotein etc. The fact that the magnetic particle bears a molecule which together with the biological entity forms a pair forming group, ensures specific binding of the two to each other.

According to the method of the present invention, the magnetic particles and the sample containing the biological entities are contacted under conditions allowing said specific binding. For example, where the pair forming group is complementary nucleic acid sequences, the conditions should be such which allow a specific hybridization, for example slightly elevated temperature, in which only complementary sequences hybridize, while non complementary sequences remain annealed. In this step, various rinsing and washing procedures can be carried out in order to eliminate non specific binding.

The magnetic particles, are now clustered utilizing magnetic force. This is typically carried out by placing inside the vessel holding the magnetic particles a magnetic field providing member having a relatively narrow end. The lines of magnetic field of said end are such which cause clustering of magnetic particles, and if these magnetic particles are bound to the biological entities carrying the fluorescent label, said clustering causes the fluorescent emission to become concentrated in distinct patches.

By a preferable mode, said clustering is carried by utilizing the device of the invention, in its activated state. In this state, the narrow tip of the device, can cause a clustering of the particles in relatively large clusters.

The final step of the method is reading that fluorescent emission of the label by a suitable instrument For example, the instrument may detect the change in wavelength from the transmitted to the emitted wave, caused by the fluorescent label. The precise wavelength shift is, of course, dependent on the fluorescent label used.

By use of the method of the present invention, a defused fluorescent signal, which is caused by the emission of a fluorescent bearing biological entities, becomes concentrated in distinct patches, thus increasing the "signal to noise" ratio, and allowing easier detection.

The method of the present invention is particularly useful for a post PCR detection as will be explained herein below.

The invention will now be illustrated with reference to some non-limiting examples and drawings:

DESCRIPTION OF SPECIFIC EMBODIMENTS

Figure 1A:
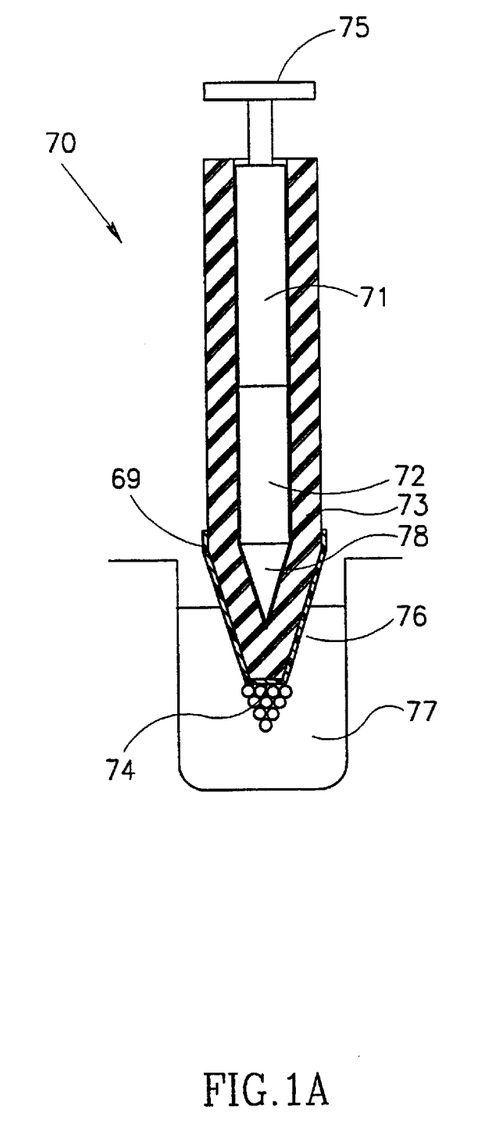
FIGS. 1A and 1B show a schematic representation of the device of the invention in a first position (1A) and a second position (1B)
Figure 1B:
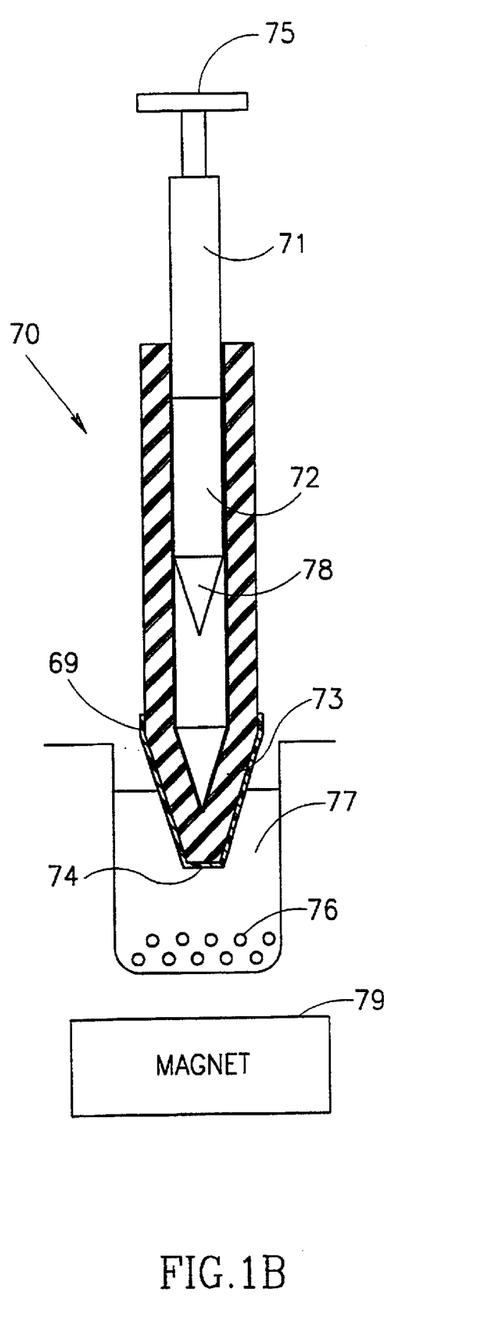

Reference is now made to FIG. 1 which shows a device in accordance with the invention 70.

The device includes an elongated member 73 made of a non-magnetic material, i.e. polypropylene, having attached a particle collecting tip 74 with tapering sides and a blunt end. Said tip 74 is covered by a disposable cover 69 so that sterility of the samples may be maintained. Slidable within the elongated member is a magnetic field providing member 71, which has a portion 72 made of magnetic material, and a tapered end 78 made of the same magnet or of a ferromagnetic material such as iron. The purpose of end 78 is to focus the lines of the magnetic field produced by portion 72 to a fine point.

The slidable member 71 can move between two positions: a first position shown in FIG. 1A in which the end 78 of magnet 72 is adjacent to a particle collecting tip 74, so that particles 76 are attracted to the truncated end of said tip 74. It is possible to construct the device so that a controlled amount of particles are picked while some particles are maintained The second position (FIG. 1B) the end 78 of magnet 72 of the magnetic field providing member, is distanced from tip 74 so that particles 76 are released from said end into the reaction vessel 77. The magnetic field providing member 71 is fitted with a handle 75 for manual displacement from the first position (1A) to the second position (1B).

The displacement may also be carried out automatically, for example with the use of an electromagnet. The automatic displacement may also be computer controlled.

It is possible to facilitate the release of magnetic particles 76 from tip 74 by bringing a magnet 79 in close proximity to the end of vessels 77. The magnet 79 may be in close proximity with the vessel, but preferably it should be brought close to the bottom of the vessel only when member 71 is displaced to the second position shown in FIG. 1B. The simultaneous movement of the member 71 away from the particles and of magnet 79 towards the particles together with vibrator causes resuspension in vessel 77 which may be advantageous for example, when rinsing the magnetic particles in the liquid, or when mixing them with various reagents or when eluting bound molecules into the liquid. The transition from the position in FIG. 1A to FIG. 1B may be for the purpose of transfer of the magnetic particles or may be solely for the purpose of rinsing/mixing the magnetic particles.

Figure 2:
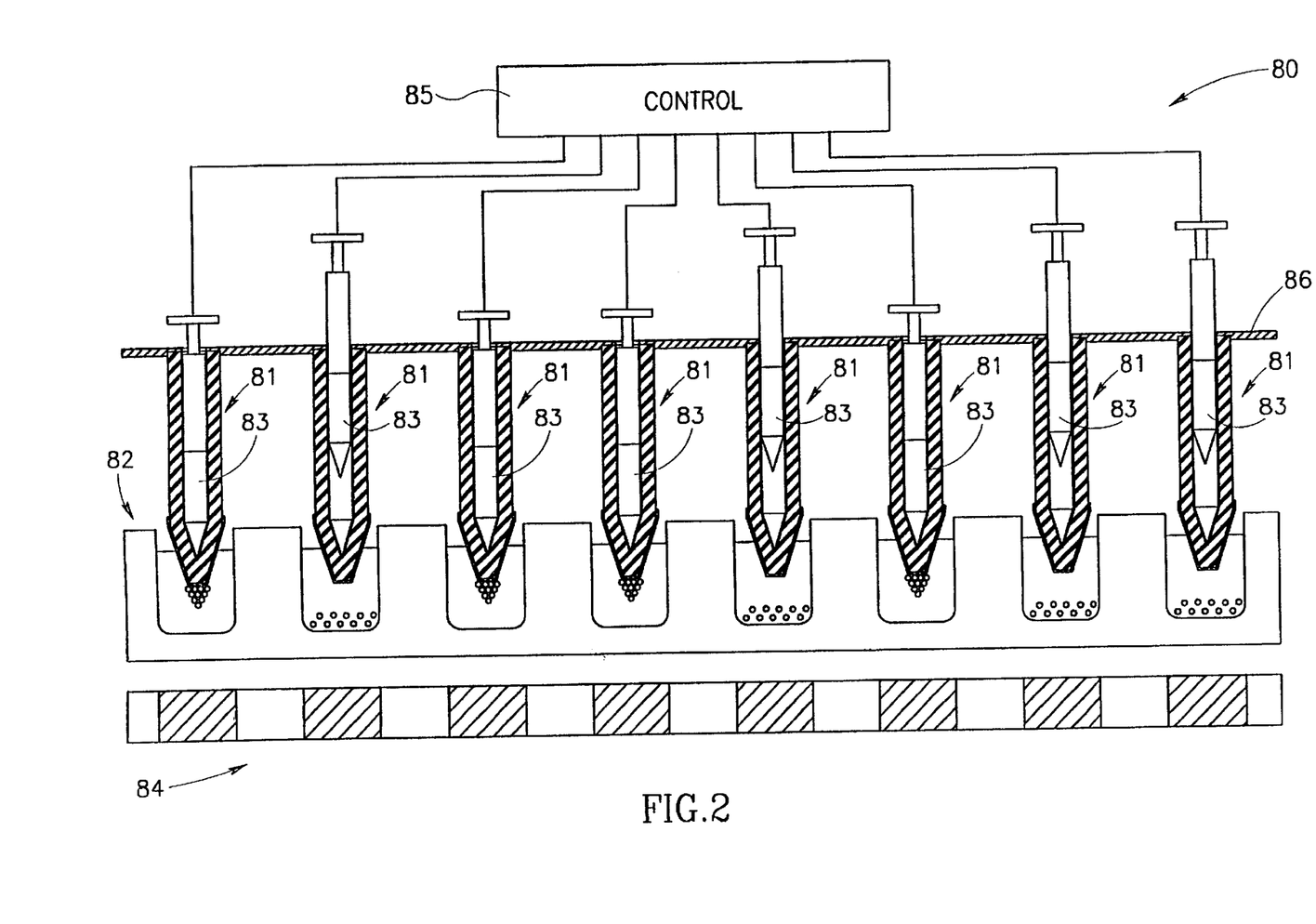
FIG. 2 shows a schematic representation of the system of the invention according to the magnetic embodiment.

Reference is now made to FIG. 2 which shows the system of the invention 80 in accordance with the magnetic embodiment The system is composed of a plurality of individual devices (collecting members) as those disclosed in FIG. 1, in the present case of eight such devices 81. For other configurations, the number of the devices may vary, and it may include twenty-five devices in a five-by-five format, ninety-six devices in a standard eight-by-twelve format, etc. Each individual device includes a magnetic field providing member 83, which may be in a lowered position, thus collecting magnetic particles, or may be in a raised position, not collecting magnetic particles, or releasing magnetic particles previously collected.

The spacing of individual devices 81 in the system 80 corresponds to the spacing, and the arrangement of the individual wells, in an array of wells 82. In the specific case, the array of wells is an array of eight wells, which is a single row in an eight-by-twelve, 96-well format of standard micro-titer plates.

For facilitation of release of magnetic particles, when member 81 is raised, an array of magnets 84, corresponding to the array of wells, may be placed beneath of wells 82. Alternatively, a single flat magnet spans the whole area of the array of wells.

Each individual device 81 is separately connected to control unit 85. Control unit 85 may raise some field providing members 83 in some devices 81 of the system, while maintaining others in their lower positions, thereby enabling collection of magnetic particles only from some wells in array 82, while the other magnetic particles remain in the well. The control may be by separate mechanical mechanism, which are controlled by a central computer, but preferably, the control is carried out by turning on and off individual electromagnets, each connected to member 83, so that turning on of an electromagnet attracts member 83 and pulls it up, thus releasing magnetic particles (or not attracting them) and turning off a specific electromagnet allows, due to gravity force, member 83 to fall down, thus enabling attraction of the magnetic particles to the particle collecting tip of each device 81.

Frame 86 holds all of individual devices 81 as a single unit. All systems 80 may be raised and transferred from one well arrangement 82 to another well arrangement for depositing of magnetic particles, or to a membrane for formation of an imprint of magnetic particles.

Individual devices 81 may be separated from the system so that they can be used separately as single devices or alternatively fitted into another system by insertion into appropriate places in the frame. For example the second, third and fifth device may be detached from frame 86 and fitted to a new and smaller frame. Such rearrangement can be advantageous in sequencing by hybridization (SBH), procedure, where smaller and smaller arrays of magnetic particles should be formed for the determination of a nucleic acid sequence.

Figure 3A:
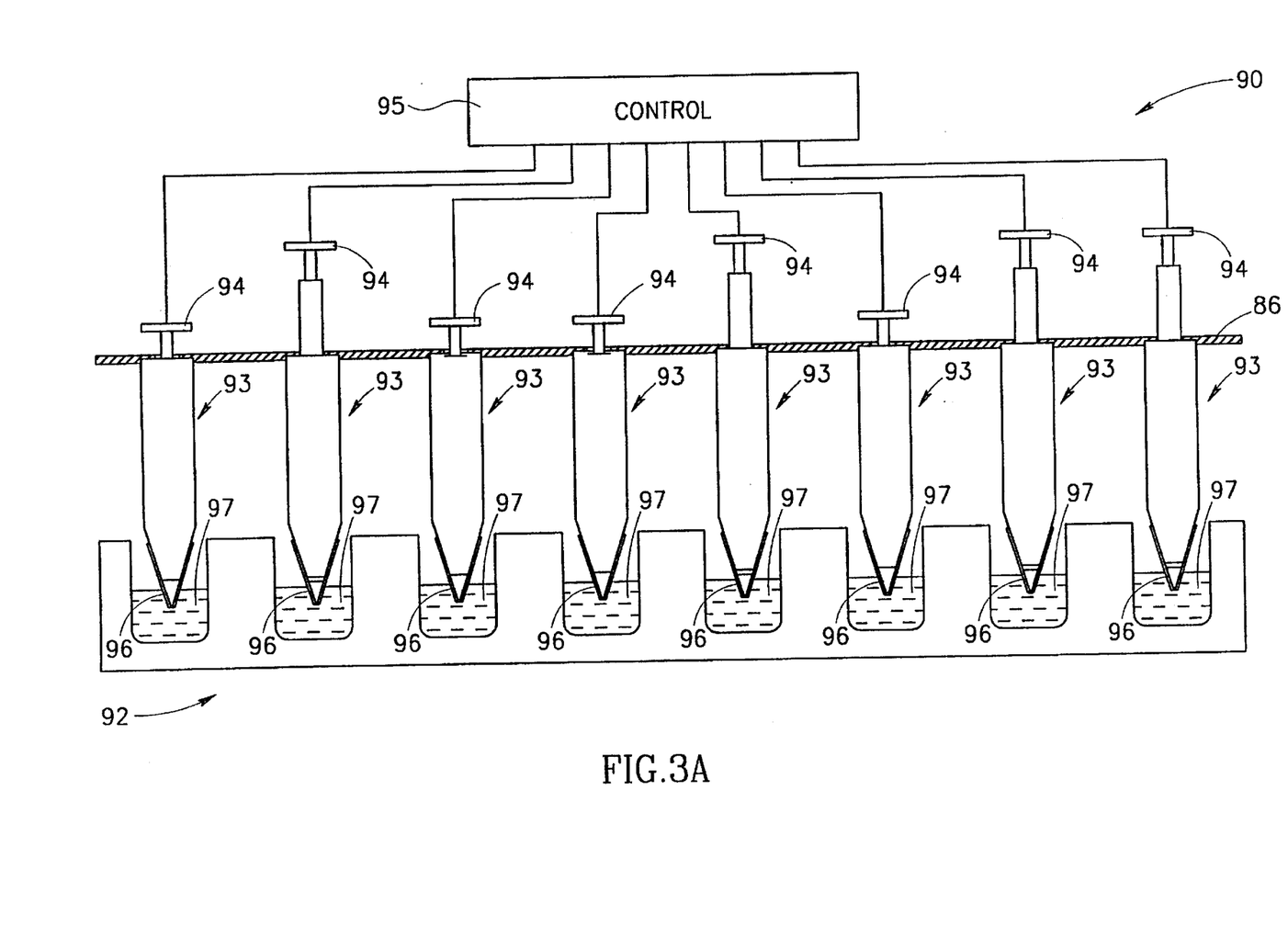
FIG. 3A and FIG. 3B shows a schematic representation of the system in accordance with the non-magnetic embodiment.

FIG. 3A shows another system of the invention 90 in accordance with the non-magnetic embodiment. The system comprises eight individual pipetors 93 capable of collecting small amounts of liquid by magnetic force. Each pipetor has a handle 94 which when raised creates a vacuum force in tip 96 drawing liquid 97 into the tip. When handle 94 is in a lowered position liquid 97 is not drawn, or previously drawn liquid is released from tip 96. The spacing and arrangement of individual pipetors 93 corresponds to the spacing and arrangement of individual wells in the vessel array 92. The activation (by raising handle 94) and deactivation (by lowering handle 94) of each pipetor 93 is controlled independently by control mechanism 95 for example a computer. The handle can be activated independently by spring mechanism. Alternatively the handle itself may be made of ferromagnetic material and is raised by an electromagnet, so that although the force created by the pipetor on the material to be transferred is vacuum, said vacuum is produced by raising the handle with the end of an electromagnet.

Figure 3B:
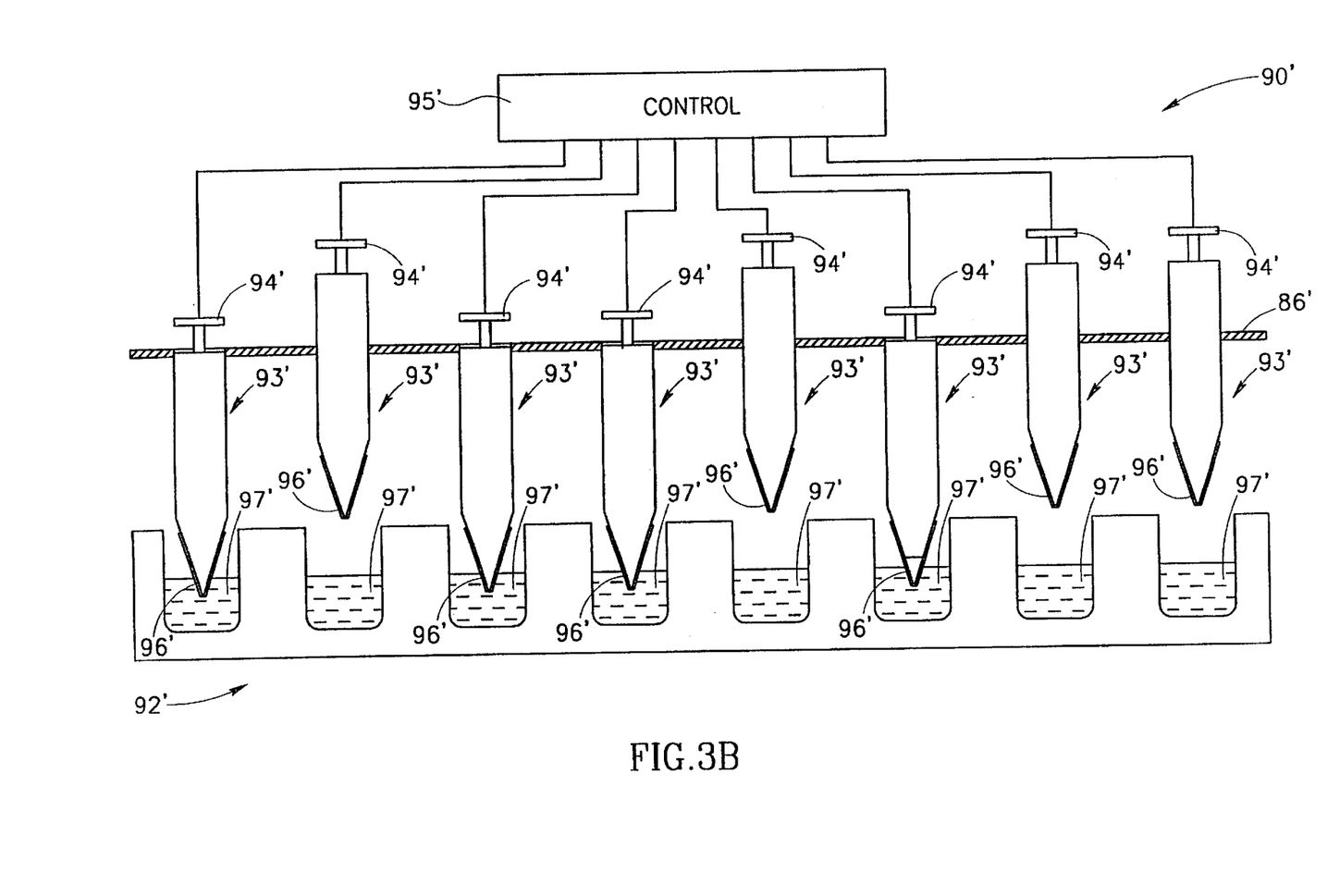

FIG. 3B shows essentially the same system as in FIG. 3A, wherein each identical component is marked with the same number as in 3A with a prime ('). Individual pipetors 94' can become deactivated, by raising the whole pipetor (not the piston) out of vessels 96' with the aid of control means 95'.

Figure 4A:
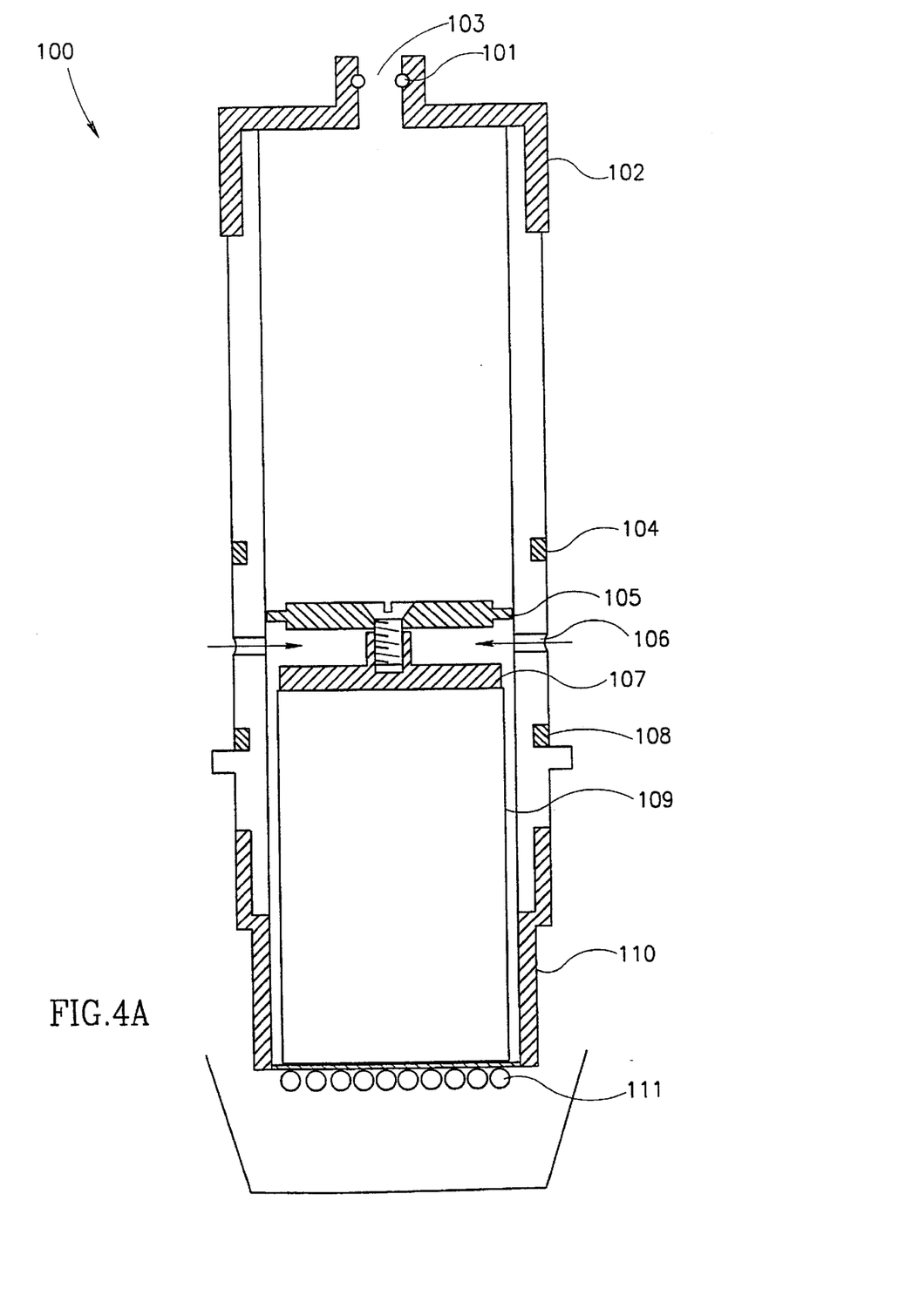
FIGS. 4A and 4B show a schematic representation of a device operated by pneumatic force in a first position 4A and a second position 4B.
Figure 4B:
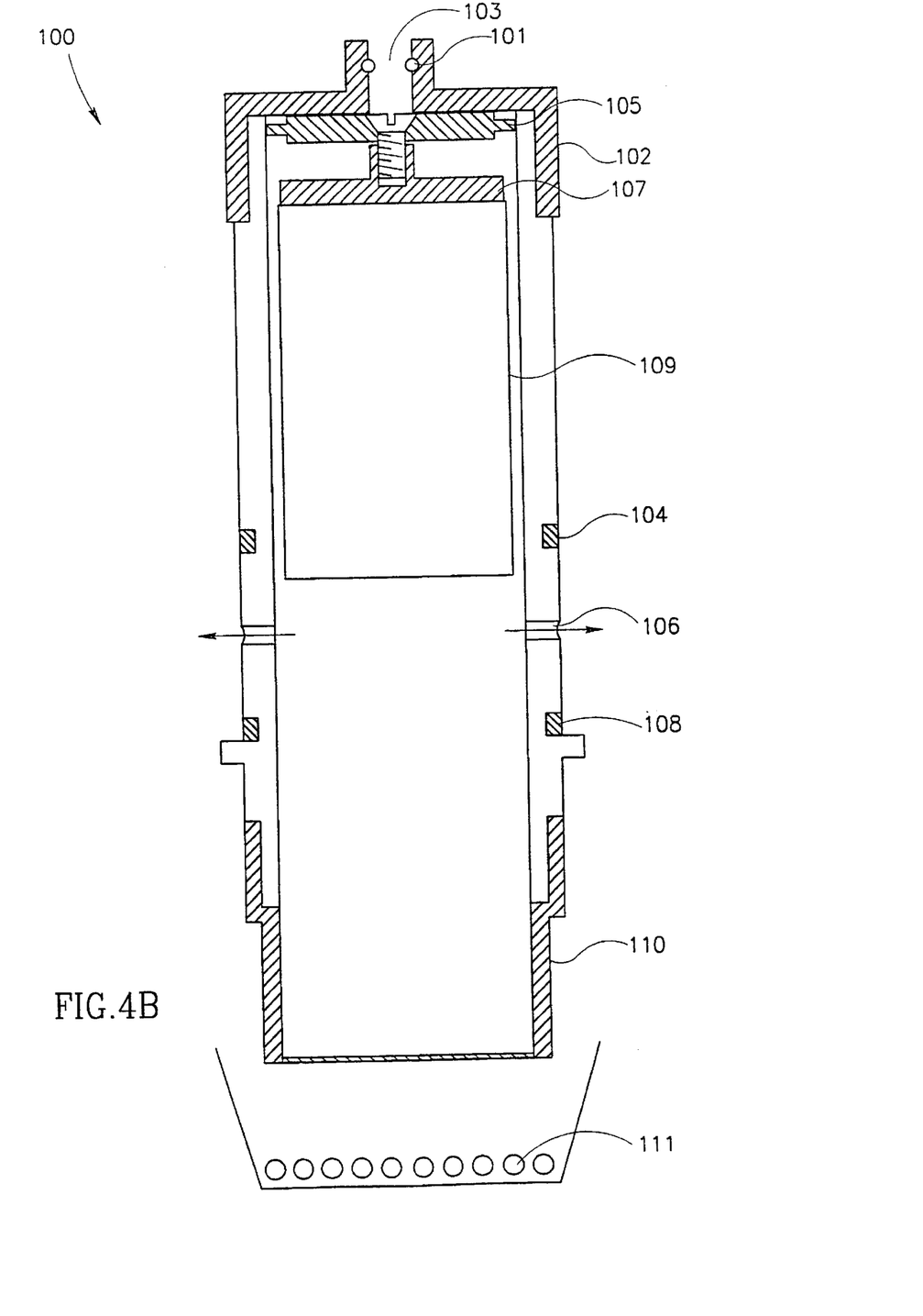

Another device 100 of the invention is shown in FIGS. 4A and 4B, while the device collects magnetic particles by magnetic force, the transfer of the collecting member through one state to the other is carried out by vacuum pressure, i.e. is activated by pneumatic forces. Device 100 consists of a magnet 109, which is slidable within the inner lumen of device 100. In FIG. 4A magnet 109 is in contact with the inner wall of a flat polypropylene tip end 110. When the magnet is in contact with this tip (FIG. 4A), magnetic particles 111 are collected by magnetic force to the tip. The magnet is held by magnetic force from an iron made ring 108. When vacuum force is applied, air moves in through opening 106, forcing piston 105 to move up. The piston 105 is connected to magnet 109 through connector 107. Thus, when vacuum force is applied (FIG. 4B), the magnet moves from its lower position shown (FIG. 4A) to its upper position. The magnet remains in the upper position (FIG. 4B) due to magnetic force applied by upper iron ring 104. In such a position as shown in FIG. 4B, magnetic particles 111 are not collected or are released back to the vessel. When air pressure is released from the pistons through upper inlet 103 magnet moves again into the position shown in FIG. 4A and particles are recollected. 101 is an O-ring used for sealing the upper inlet when vacuum force is applied. 102 is an upper closure of device 100.

Optionally, an ultrasonic vibrator can be attached to a 96-well microplate, and this permits resuspension of magnetic particles in the well.

EXAMPLE 1

Collection and Transfer of Magnetic Particles with the Device of the Invention

A. Materials and Tools

The magnetic particles' suspensions used was 1 mg/ml and 2 mg/ml (BioBeads Merck). The magnetic plate for 96-well microplates was manufactured by PerSeptive Bio-System and used with a 96-well polypropylene microplate. The magnetic device of the invention (Bio-Magnetics) had a cylindric magnet 4 mm diameter and length 20 mm (NdFeB—N40/Ni from Magma). The polypropylene tips used as disposable tips had flat ends of different thickness 30, 50 and 90$\mu$ (micrometer). The microscope slide used for counting of particles was Bright-line Hemacytometer. Microscope was B×60, Olympus. The buffer used was 1×SSC.

B. Experimental Procedures

Three wells in the polypropylene plate were loaded with 0.1, 0.15 and 0.2 ml buffer and three adjacent wells were loaded with 0.1, 0.15 and 0.2 ml of 1 mg/ml magnetic particles suspension (stock suspension). The polypropylene tip with flat end of 90 micrometer was attached on end side of the magnetic device of the invention.

The device was held over a well No. 1 containing the suspension (0.1 ml) (the magnet contacts the inner side of the 90 micrometer flat tip) and moved so it gently touched the suspension surface for one minute. Magnetic particles moved towards the tip and created a "button" composed of a cluster of magnetic particles. As a result the suspension became clear. Next, the device is taken out of the well, and the microplate is put on the flat magnet in order to facilitate detachment of the particles from the device re-suspension of the collected magnetic particles to the wells.

In order to move the cylindric magnet to the second position (where the magnet is distanced from the particle collecting end) by magnet force an iron rod was placed inside the device.

Then the device was brought over a well with 0.1 ml buffer so that the flat tip was gently touching the buffer. Particles moved down into the buffer with the aid of magnetic field from the flat magnet in less than a minute.

The remaining particles in well No. 1 were mixed with a pipette and a 0.05 ml sample was taken from the homogeneous solution and put on a cell counting glass. the results are shown in the following Table 1:

TABLE 1

| No. | Thickness of tip | Stock concentration | Stock volume | Buffer volume | m.p. remaining in $10^{-4}$ ml | m.p. in stock in $10^{-4}$ ml | Efficiency of device % |
|---|---|---|---|---|---|---|---|
| 1 | 30μ | 1 mg/ml | 100 μl | 100 μl | 0.2 | 1000 | 99.98 |
|   |     |         | 150 μl | 150 μl | 1   |      | 99.90 |
|   |     |         | 200 μl | 200 μl | 0.8 |      | 99.92 |
| 2 | 50μ | 1 mg/ml | 100 μl | 100 μl | 0.8 | 1000 | 99.92 |
|   |     |         | 150 μl | 150 μl | 3   |      | 99.70 |
|   |     |         | 200 μl | 200 μl | 5.4 |      | 99.46 |
| 3 | 90μ | 1 mg/ml | 100 μl | 100 μl | 16.7 | 1000 | 99.33 |
|   |     |         | 150 μl | 150 μl | 5   |      | 99.50 |
|   |     |         | 200 μl | 200 μl | 7.2 |      | 99.28 |
| 4 | 30μ | 2 mg/ml | 100 μl | 100 μl | 0.4 | 2000 | 99.98 |
|   |     |         | 150 μl | 150 μl | 3.33 |     | 99.83 |
|   |     |         | 200 μl | 200 μl | 3   |      | 99.85 |
| 5 | 50μ | 2 mg/ml | 100 μl | 100 μl | 1.8 | 2000 | 99.91 |
|   |     |         | 150 μl | 150 μl | 3.4 |     | 99.83 |
|   |     |         | 200 μl | 200 μl | 0.4 |     | 99.98 |
| 6 | 90μ | 2 mg/ml | 100 μl | 100 μl | 5.33 | 2000 | 99.73 |
|   |     |         | 150 μl | 150 μl | 12.4 |     | 99.38 |
|   |     |         | 200 μl | 200 μl | 6.4 |     | 99.68 |

For determination of magnetic particles counting under the microscope took place. The efficiency of the magnetic device is calculated according to the formula: % yield= 100%* (remaining m.p. in 50 μl after collection)/(m.p. in 50 μl stock suspension)

Efficiency of device=100%—% yield (efficiency means % of transferred m.p.).

The above experiment was repeated under the following conditions:

with 0.15 and 0.2 ml suspension
with 30 and 50 micrometer thick tip and
with 2 mg/ml particle suspension

EXAMPLE 2

Use of the System of the Invention for Creation of a Peptide Library by Combinatorial Chemistry

Materials

1. Four polypropylene 96-well microtiter plates (Nunc, Denmark) containing four different amino acids depicted schematically as (A, B, C, D) blocked at the amino end by tertbutyloxycarbonyl (Boc) Group, (each plate contains one amino acid in approximately 16 pmol per well) together with dicyclohexylcarbodiimide in a total volume of 200 μl per well.
2. 96-well microtiter plate with magnetic particles suspensions, 200 μl per well (200 μg particles). The particles are used as solid phase for peptide synthesis based on the Merrifield method.
3. 96-well microtiter plate with 50 per cent trifluoroacetic acid in dichloromethane, 200 μl per well.
4. 96-well microtiter plate with diisopropyl ethyl amine, 200 μl per well.
5. 96-well plate with 200 μl HF per well.
6. A system of 96 magnetic devices (or pins) corresponding to 96-well format. This is Bio-Magnetics unique combinatorial system (or combinatorial pin device).

Experimental Procedures

Step 1

1. The first amino acid (20 pmol/mg magnetic particles) is already bound to the magnetic particles via their carboxyl end and the amino group is masked (or blocked) with a protecting group. The system of 96 pins is used to collect simultaneously magnetic particles from 64 wells and transfer them to a plate with 50% trifluoroacetic acid in dichloromethane. The Boc Group is completely removed, with minimal loss of the other protecting groups.
2. The system of 96 pins is used to collect particles from all the 64 wells and transfer them to a plate with diisopropyl ethyl amine. This tertiary amine neutralizes the α-amine salt (created in step 1) and the free amine of the bound amino acid is then ready to couple with a second Boc-amino acid.

As a result is created 64 wells all containing the same amino acid.

```
─────────────────────────────
            64 wells
─────────────────────────────
```

Step 2

3. The system of 96 pins is used to collect particles from 16 wells and transfer them to 16 wells in a plate containing amino acid A. The second group of particles are transferred from 16 wells to 16 wells in a plate containing amino acid B. The third group of particles are transferred to 16 wells in a plate containing amino acid C. The fourth group of particles are transferred to 16 wells in a plate containing amino acid D. In each of the four plates the dicyclohexylcarbodiimide activates the coupling reaction. The result is four groups of different dipeptides, each group containing 16 dipeptides. As a result 4 different groups consisting of 16 wells are created.

```
─────────────────────────────
       A          |     B
   16 wells
       C          |     D
─────────────────────────────
```

4. Magnetic particles from all 64 wells (the four groups) are collected via the 96 pin system (device) and transferred to a plate containing trifluoroacetic acid in dichloromethane.

5. Magnetic particles from 64 wells are collected with the 96 pin system and transferred to 64 wells in a plate containing diisopropyl ethyl amine.

Step 3

6. Each group of 16 wells is divided to four subgroups (each subgroup of four wells). Using the 96 pin system magnetic particles from each subgroup are transferred to a plate with different amino acid. One subgroup to amino acid A, the second subgroup to amino acid B, the third subgroup to amino acid C, the fourth subgroup to amino acid D. In fact the 96 pin system collects simultaneously four subgroups, each one corresponding to a different group of 16 wells (See No. 3). The result is 16 different tripeptides in each group of four wells.

|   | A | B | A | B |
|---|---|---|---|---|
| 4 wells | D | C | D |
|   | A | B | A | B |
|   | C | D | C | D |

Step 4

7. Steps 4 and 5 are repeated.
8. Each subgroup contains four wells with the same tripeptides. The 96 pin system collects particles simultaneously from 16 wells (each well from a different subgroup) and transfers them to a plate containing amino acid A. Particles from 16 other (each well from a different subgroup) wells are collected via the 96 pin system and transferred to a plate containing amino acid B. The same action is done with the rest 32 wells to transfer them to plates with amino acid C and D. The results are 64 different tetrapeptides bound to magnetic particles.

|   | A | B | A | B |
|---|---|---|---|---|
|   | C | D | C | D |
| well |   |   |   |   |

9. If needed the peptides can be separated from the particles. This can be done by transferring the particles to a plate containing a strong anhydrous acid HF. Then the particles can be collected leaving the peptides in solution.

To Summarize

In the Mix-and-split method the resulting peptide libraries are mixed libraries. The new method of Example 3 permits creating ordered libraries where the location of each peptide is known. An ordered library can save work and time when detecting unknown peptide in a mixed library.

EXAMPLE 3

Post PCR Detection

Figure 5:
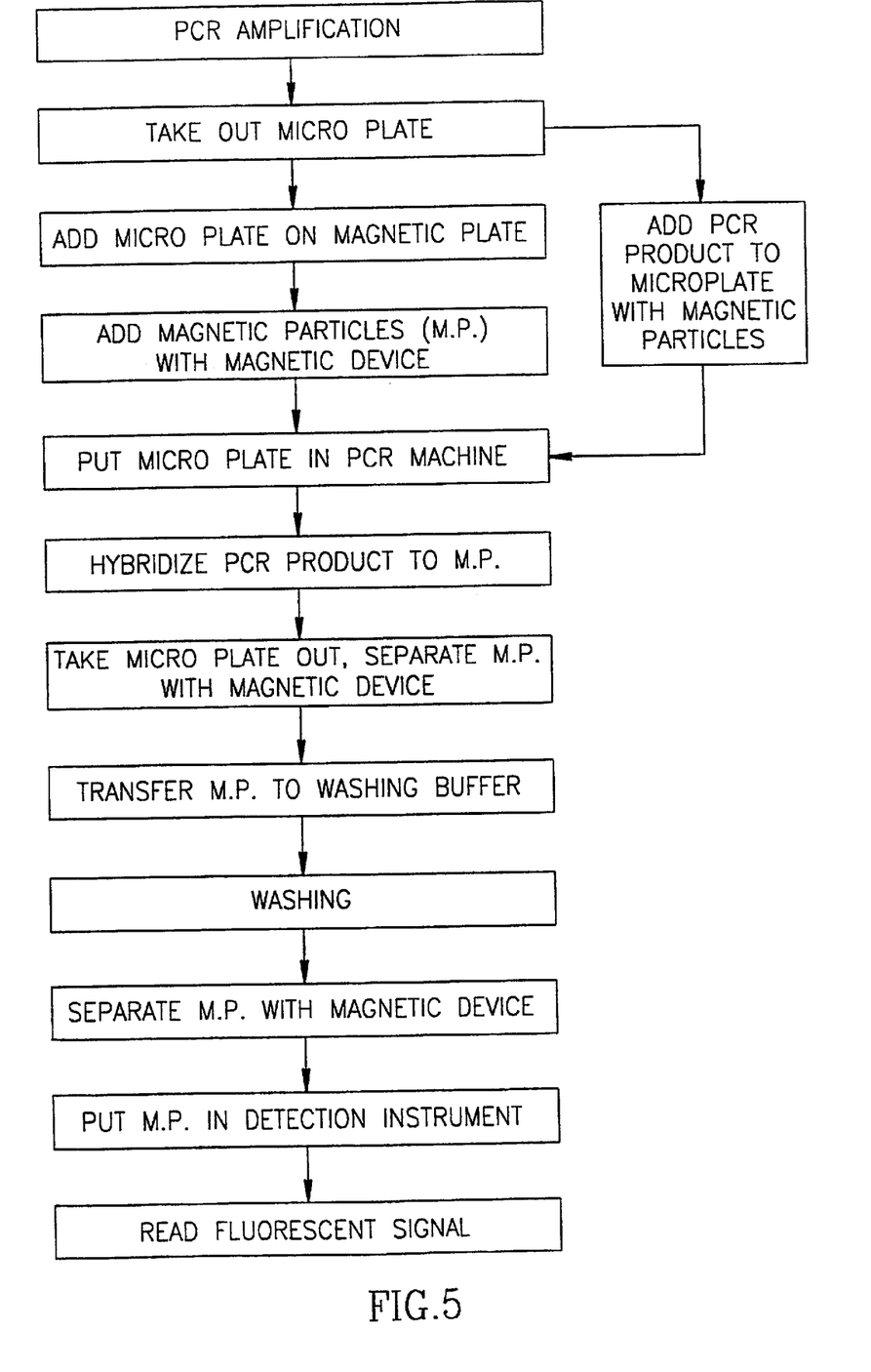
FIG. 5 and FIG. 6 show flow charts for using magnetic beads for post-PCR detection and FIG. 7 shows products of PCR amplification carrying fluorescent labels, concentrated on magnetic particles).
Figure 6:
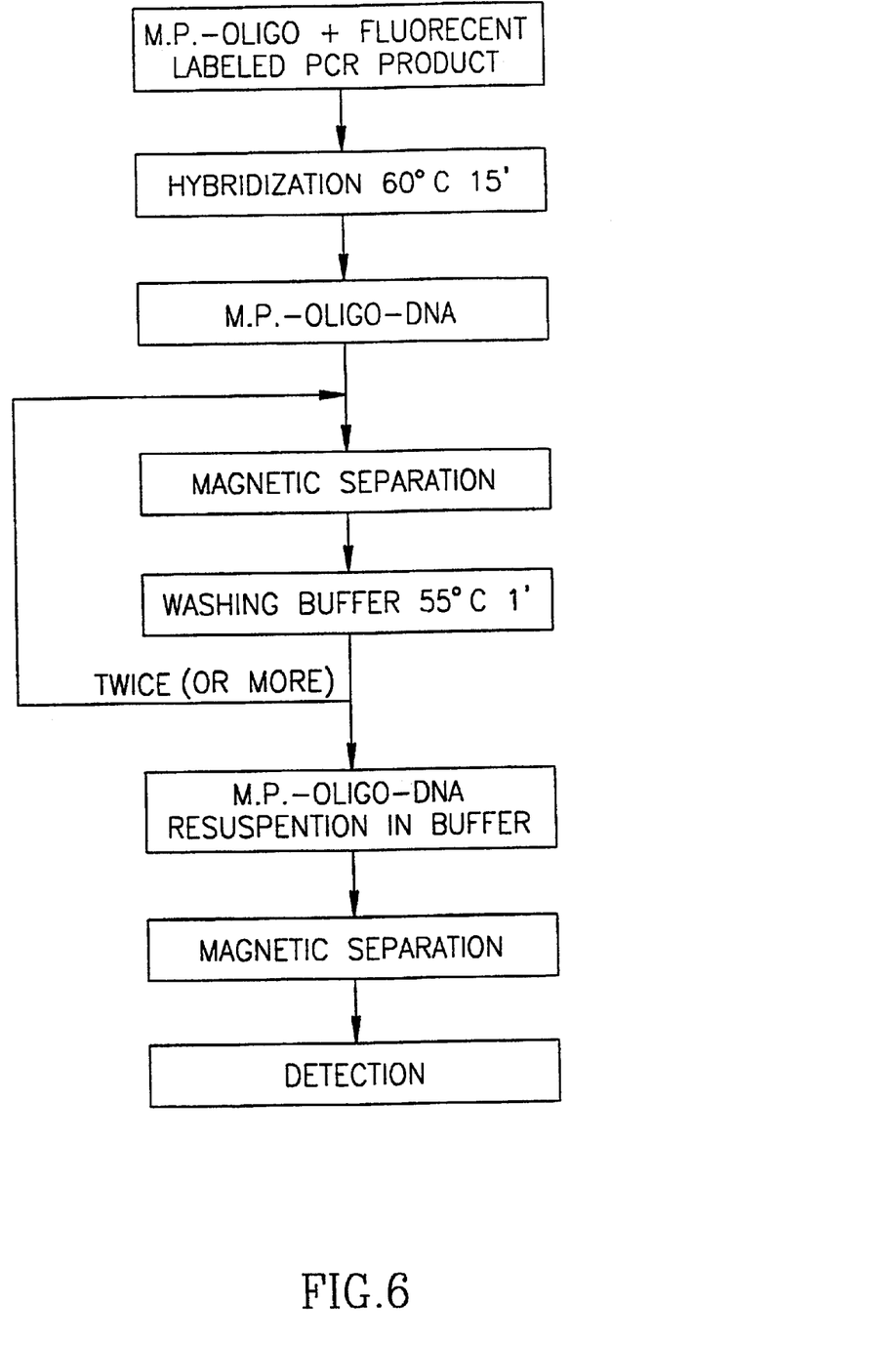

The schematic flow charts for carrying out the detection method of the invention are shown in FIGS. 5 and 6.

A. Materials

I Template
  PCR Fragment of 152 bp of the Exon 6 of Human amiloride-sensitive epithelial sodium channel beta subunit gene.

II Oligonucleotides:
  a. E1: biotin-10dT-aagcaacccctctaaacacag (SEQ ID NO:1), which was used as forward primer in amplification of the template;
  b. E2: biotin-10dT-aggcgtgcaccaccttcccac (SEQ ID NO:2), which was used as reverse primer in amplification of the template;
  c. C1: biotin-10dT-cctgaaccgctctatacacag (SEQ ID NO:3), a control to E1
  d. C2: A control of BioBeads Streptavidin, without bound oligonucleotides.
  All the oligonucleotides were synthesized in BTG Israel.

III Magnetic particles:
  BioBeads Streptavidin from Merck, 10 mg/ml with a binding capacity for biotinylated oligonucleotide of 400 pmol/1 mg full capacity or 20 pmol/50 µg.

B. Experimental Procedures

IV Coupling of oligonucleotides to BioBeads:
  300 µg/ml oligonucleotides were dissolved in 20 mM Tris-HCl buffer pH 8.0 and were diluted in binding buffer (Dynal 2M NaCl, 1 Mm EDTA, 10 mM Tris-HCl pH 7.5) and added to 100 µg magnetic particles (m.p.). The coupling reaction was carried out at 37° C. for 30 min. with continuous shaking. 50 µg of magnetic particles were coupled with 0.1 pmole of oligonucleotides.

V Fluorescent Labeling of PCR product/template:
  AMCA-6-dUTP (Amino-methylcoumarin-6-2'-deoxyuridine-5'-triphosphate) from Boehringer Mannheim was used to label the template DNA in a PCR. The PCR product was further analyzed by PAGE to verify amplification. 1–20 µl of PCR product were used in different hybridization reactions.

VI Hybridization on magnetic particles (M.P.)
  30 µg of magnetic particles were prehybridized in 8 µl of hybridization buffer at 45° C. for 20', Hybridization buffer contained: 5×SSC pH 7, Sambrook, Fritsch & Maniatis MOLECULAR CLONING: A LABORATORY MANUAL 1989 2/E and 0.25 SDS. Hybridization of 2 µl fluorescent PCR product to the immobilized oligonucleotides on the m.p. was carried out at 60° C. for 5', 15', 45' and 60'. Following hybridization the supernatants were decanted, and the particles were washed with wash buffers: once with 5×SSC buffer containing 0.2% SDS at 55° C., twice with 1×SSC buffer containing 0.2% SDS at 55° C. and once with 1×SSC buffer at 65° C. At the end of the experiment the m.p. were resuspended in 1×SSC buffer at a concentration of 1 µg/µl and 1.0 µl was then analyzed under fluorescent microscope.

C. Results (i) Fluorescence Microscopic Observations:
  Surface fluorescence on the magnetic particles was assessed using B×60 Olympus Microscope with 100 W Hg lamp 330–385 mm Excitation filter, DM 400 Dichroic mirror, BA 420 barrier filter.

(ii) Effect of Temperature on Hybridization
  Hybridization at lower temperature of 42° C. and 55° C. with subsequent washing at 4° C. did not give adequate specific binding. Hybridization at 60° C. was successful in getting fluorescent positive signal. Washing the particles at higher temperature than that of hybridization itself further substantially reduced the background of non-specific binding.

(iii) Effect of Concentration of Immobilized Oligonucleotide on m.p.
  Our observations suggested that when magnetic particles were coupled to the oligonucleotides at 100% binding capacity (20 pmol/50 μg m.p.) or 50% binding capacity (10 pmol/50 μg m.p.); the hybridization reaction was not successful. We observe absolute no fluorescently labeled particles or undetectable fluorescence on the particles. We suggest this could be due to the steric hindrance created by the bound oligonucleotides on the particles. When the same samples were analyzed with visible transmitted light to get pictures of the aggregates.

References:

1. Immobilization of polynucleotides on magnetic particles, Philip J. R. Day, Pargat S. Flora, John E. Fox and Matthew R. Walker, *Biochem. J.* 278:735–740, (1991).

---

SEQUENCE LISTING

<160> NUMBER OF SEQ ID NOS: 3

<210> SEQ ID NO 1
<211> LENGTH: 21
<212> TYPE: DNA
<213> ORGANISM: Human

<400> SEQUENCE: 1
aagcaacccc tctaaacaca g          21

<210> SEQ ID NO 2
<211> LENGTH: 21
<212> TYPE: DNA
<213> ORGANISM: Human

<400> SEQUENCE: 2
aggcgtgcac caccttccca c          21

<210> SEQ ID NO 3
<211> LENGTH: 21
<212> TYPE: DNA
<213> ORGANISM: Human

<400> SEQUENCE: 3
cctgaaccgc tctatacaca g          21

--- amount of bound oligonucleotides was reduced to 1 pmol/50 μg m.p. and 0.1 pmol/50 μg m.p. a significant increase in number of fluorescently labeled magnetic particles was observed. This effect was although more obvious with the 0.1 pmol/50 μg m.p.

(iv) Effect of the Poly(T) Spacer on Hybridization

Oligonucleotides bound without spacer (linker arm) gave negative results. However, use of 10(dT) linker gave adequate binding to the template DNA.

(v) Effect of Magnetic Concentration

The presence of SDS during hybridization (0.25 % SDS) and subsequent washing (0.2% SDS) improved specific binding conditions.

(vi) Effect of Magnetic Concentration

Figure 7:
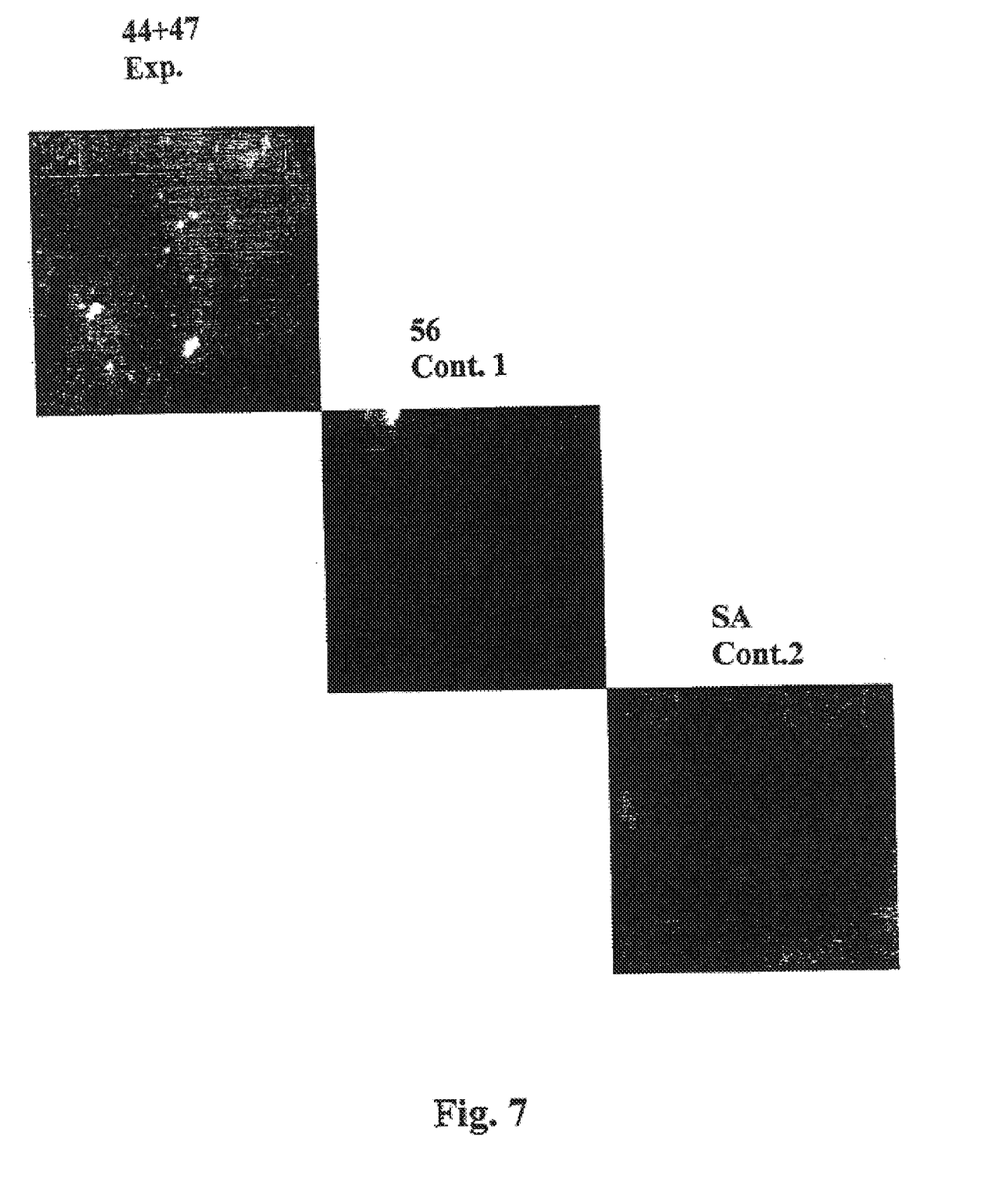

Positive fluorescent signals, mean that part of the magnetic particles are fluorescent and the others are black/brown. Sometimes if the number of fluorescent particles is low compared to the black particles it is preferable to magnetically concentrate the particles. The aggregate of particles permits getting a stronger fluorescent signal (compared to dispersed particles). Following are CCD Camera photographs of magnetic particles aggregates. In FIG. 7 the upper photograph is blue fluorescent emission from thousands of particles after specific hybridization of 60' in 60° C. Control 1 (Con 1) and Control 2 (Con 2) gave no emission, because non specific binding did not occur. In page 2

What is claimed is:

1. A system for transfer of solid magnetic particles from a plurality of source vessels to a plurality of target vessels such that material from each source vessel is transferred to a designated target vessel, the system comprising a plurality of detachably connected collecting members permitting simultaneous transfer of solid particles from a number of source vessels to one or more target vessels; each collecting member is made of a material which is not affected by a magnetic field, having a truncated particle collecting tip and an elongated lumen with an open end, said end of the lumen being at a distal portion of said elongated member adjacent to said tip; the lumen accommodating a magnetic field providing member within the lumen, which member is displaceable between a first position in which the magnetic field providing member is in said distal portion whereby attraction of said particles to said truncated tip occurs, and a second position in a proximal portion of said lumen in which said particles are not attracted to said truncated tip, transition between the first position and the second position is controlled by electric or pneumatic force; each collecting member is independently controlled.

2. A system according to claim 1, further comprising a computer for controlling the independent transition from said first position to said second position of each collecting member.

3. A system according to claim 1, wherein the first position is obtained by application of a force capable of creating a magnetic field in the truncated tip of each collecting member and the second position is achieved by ceasing of creation of said magnetic field.

4. A system according to claim 3, wherein the magnetic field is created by the use of an electromagnet present in each collecting member.

5. A system according to claim 3, wherein the magnetic field is created by the use of a pneumatic pump.

6. A system according to claim 3, wherein the magnetic field is created by the use of a spring.

7. A system according to claim 1 for the quantitative collection of magnetic particles attracted to the truncated tip, wherein the proportion of particles collected is in correlation to the time of collection.

8. A system for quantitative collection of magnetic particles according to claim 7, wherein the truncated tip thickness is less than 30 $\mu$m.

* * * * *